United States Patent [19]

Debbas

[11] Patent Number: 4,966,583
[45] Date of Patent: Oct. 30, 1990

[54] APPARATUS FOR LOCATING A BREAST MASS

[76] Inventor: Elie Debbas, 800 Southern Ave., SE #407, Washington, D.C. 20032

[21] Appl. No.: 305,965

[22] Filed: Feb. 3, 1989

[51] Int. Cl.⁵ ............................................. A61M 29/02
[52] U.S. Cl. ..................................... 604/98; 606/192
[58] Field of Search ..................... 604/96, 103, 97, 98, 604/99, 100, 101, 102; 606/192, 193, 196, 197, 159, 185, 194; 128/753, 754

[56] References Cited

U.S. PATENT DOCUMENTS

| | | |
|---|---|---|
| 2,001,638 | 5/1935 | Tornsjo . |
| 2,705,949 | 4/1955 | Silverman . |
| 3,154,077 | 10/1964 | Cannon .......................... 604/101 X |
| 3,515,137 | 6/1970 | Santomieri . |
| 3,598,119 | 8/1971 | White . |
| 3,634,924 | 1/1972 | Blake et al. ..................... 604/103 X |
| 3,833,003 | 9/1974 | Taricco . |
| 3,890,970 | 6/1975 | Gullen . |
| 4,007,732 | 2/1977 | Kvavle et al. . |
| 4,571,239 | 2/1986 | Heyman . |
| 4,682,606 | 6/1987 | DeCaprio . |

FOREIGN PATENT DOCUMENTS

| | | | |
|---|---|---|---|
| 2477005 | 9/1981 | France | ................................... 604/97 |
| 2480127 | 10/1981 | France | ................................. 604/101 |

Primary Examiner—Michael H. Thaler
Attorney, Agent, or Firm—Burns, Doane, Swecker & Mathis

[57] ABSTRACT

A mass localization device includes a catheter and a needle. The catheter includes inner and outer walls spaced from each other and creating a gap between the walls extending along substantially the entire length of the catheter. The distal portion of the outer wall includes an inflatable balloon. A port extension member is provided at the proximal end of the catheter for communicating a supply of air to the inflatable balloon via the gap between the inner and outer walls of the catheter. The needle is insertable through the catheter to extend beyond the distal end of the catheter. In use, the combination of the needle and catheter are inserted into body tissue. Under assistance of x-ray radiography, the device is moved toward a mass in the tissue. Once proximate the mass, an anesthetizing agent is introduced to the tissue through the needle. Subsequently, the balloon is inflated for contacting the mass, and thus making the mass palpable. The needle is withdrawn from the catheter, and the patient is prepared for a biopsy or other medical procedure. An incision to the mass can be achieved by the shortest possible distance since the mass is made palpable.

8 Claims, 2 Drawing Sheets

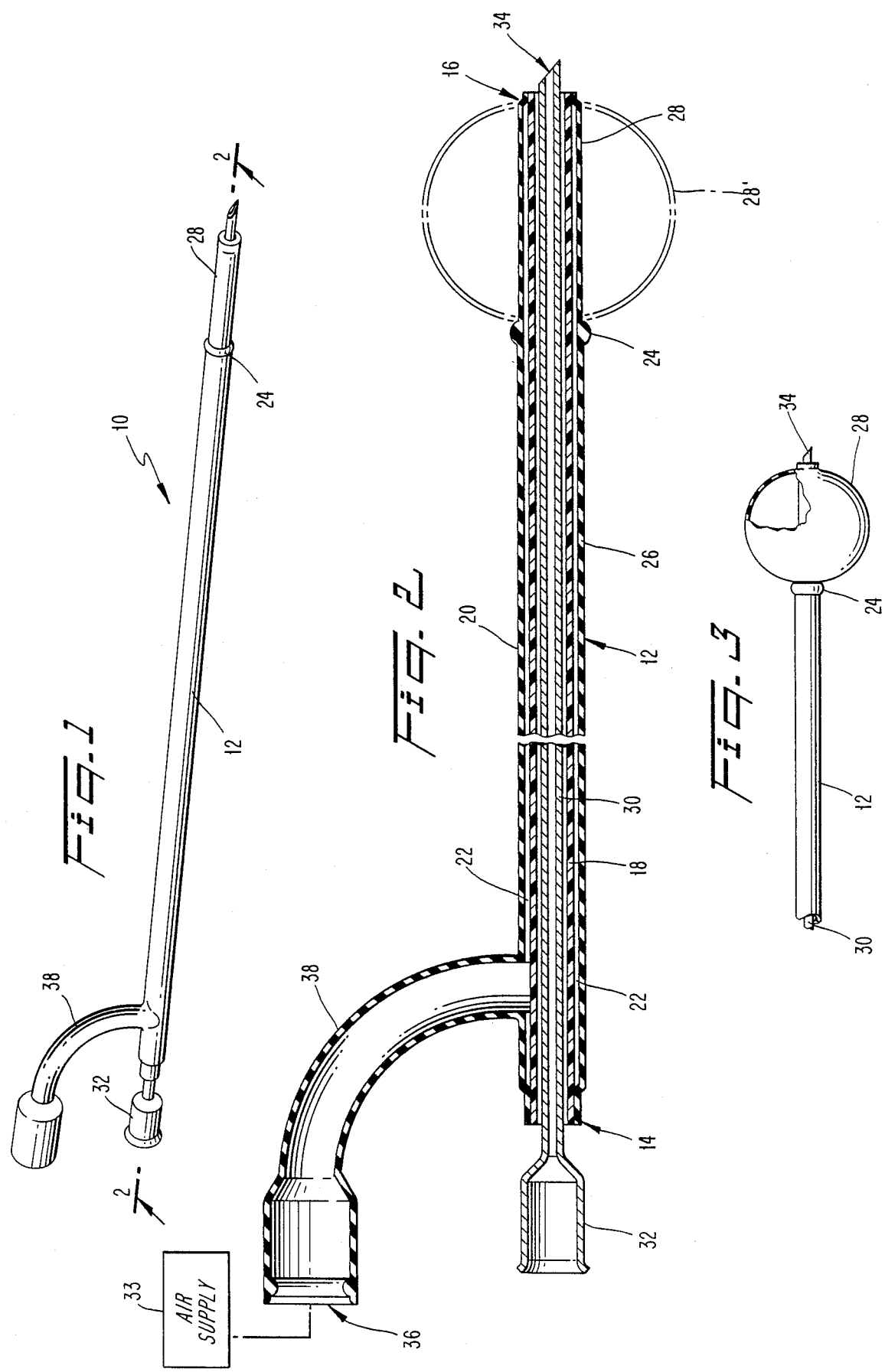

APPARATUS FOR LOCATING A BREAST MASS

FIELD OF THE INVENTION

The present invention relates to a medical instrument for locating a mass in body tissue so that the mass may be accessed or removed by the most direct incision from the epidermal layer to the mass.

BACKGROUND OF THE INVENTION

Locating masses or tumors in human tissue is necessary for a biopsy of the suspicious mass and subsequent removal. Sometimes, it is possible to locate a mass merely by touching the skin above and around the suspicious area. However, often the mass is too small to be noticed by hand or is located in fatty tissue that interferes with determining the precise location of the mass. A specific example of the latter case is the location of small breast masses or calcifications.

Typically, the precise location of these types of masses can only be determined by x-ray analysis, using specialized instrumentation prior to a surgical operation to locate the mass to be removed. Typically, a very thin needle is inserted into the breast down to the mass under x-ray control (mammography). Once it is determined by x-ray control that the tip of the needle is located at the mass site, the patient is transported to an operating room, where the surgeon creates an incision in the breast by following along the path of the inserted needle with a scalpel until reaching the mass. This method often involves a very long incision and increases the risk of post-operative infection.

An alternate method of creating an incision to gain access to or remove a breast mass is to study x-rays of the breast mass taken from various angles. Based upon experience and notional extrapolation of the views from different angles of the breast mass, an incision is made in an attempt to cut along the most direct path to the mass.

Several devices exist for localizing masses in human tissue. See, for example, U.S. Pat. Nos. 4,682,606 to DeCaprio, 3,890,970 to Gullen, and 3,598,119 to White.

The DeCaprio patent discloses a surgical needle which is inserted into a located mass and encircled by a cork screw device. The cork screw device is twisted around the mass until the tip of the worm of the screw is just beyond the furthest side of the mass. Thereafter, the handle of the cork screw device is withdrawn and a guiding extension rod is replaced to direct the surgeon to the depth of the mass in the patent's tissue. Then, a cutting instrument is inserted over the extension rod for removing the mass from the tissue.

The Gullen patent discloses a surgical cannula for delivery of paracervical anaesthesia. The cannula includes a catheter having a closed distal end with a perforated membrane. The distal end is firm and sharp enough to be inserted into body tissue to a predetermined depth, as limited by a stop member. A thin membranous ballooning portion is provided proximate the distal end of the catheter for expansion upon application of a fluid pressure within the catheter to lock the cannula in place in the tissue. The device is left in the tissue of the patient by the ballooning portion to provide periodic supply of fluid anaesthesia during a surgical procedure.

Similar to the patent to Gullen, the White patent discloses a medical instrument for use in gynecological procedures to allow the administration of a paracervical block, continuously or intermittently, with only a single placement. The device comprises an elongated hollow tube having an open distal end and receiving a needle for guiding the device into tissue. An inflatable bladder is provided near the distal end of the hollow tube for retaining the device in the tissue and minimizing trauma associated with the procedure.

The prior art devices discussed above provide a procedure for retaining a catheter type instrument in the tissue of a patient, but fail to provide a procedure for precisely identifying a mass within the tissue. Moreover, the prior art devices are of an insufficient size to accurately locate a mass within breast tissue prior to surgery.

SUMMARY OF THE INVENTION

It is a primary object of the present invention to provide a device for accurately locating a mass within breast tissue prior to a surgical procedure for taking a biopsy of, or removing the mass.

The device of the present invention comprises a catheter having proximal and distal open ends for receiving a hollow needle insertable into the catheter. An inflatable balloon is provided at the distalmost end of the catheter for expansion around the catheter at the distal end of the catheter. A source of air is connected to the catheter adjacent the proximal end of the catheter, and has a separate port connection to the catheter.

Preferably, the inflatable balloon is formed as an outer layer or sheath extending along the length of the catheter. The distalmost end of the outer layer forming the inflatable balloon has a smaller thickness than the remainder of the outer layer. As such, upon supply of air, the distal end of the outer layer expands, while the remaining portion of the outer layer remains flush with the periphery of the catheter.

With the balloon deflated and flush with the periphery of the catheter, a hollow needle is inserted to extend beyond the distal end of the catheter, and the device is inserted into the tissue to a position adjacent the mass to be located. Typically, this is performed under the control of x-ray (mammography) to precisely locate the mass. Once the mass is located and the combined catheter and needle is moved adjacent to the mass, local anesthetic is applied through the needle to the tissue area surrounding the mass, and the balloon is then inflated to identify the location of the mass. The inflated balloon is felt by the surgeon to determine the location of the mass.

The above and other objects of the present invention will become more apparent when reference is made to the following description, taken in conjunction with the accompanying drawings.

BRIEF DESCRIPTION OF THE DRAWINGS

FIG. 1 is a perspective view of the mass localization device of the present invention.

FIG. 2 is a cross sectional view taken through line 2—2 of FIG. 1 and illustrating the inflatable balloon of the localization device in both inflated and deflated states.

FIG. 3 is a partial sectional view of the mass localization device of FIG. 1, and illustrating the inflatable balloon in its inflated state.

DESCRIPTION OF THE PREFERRED EMBODIMENTS

Figure 4:
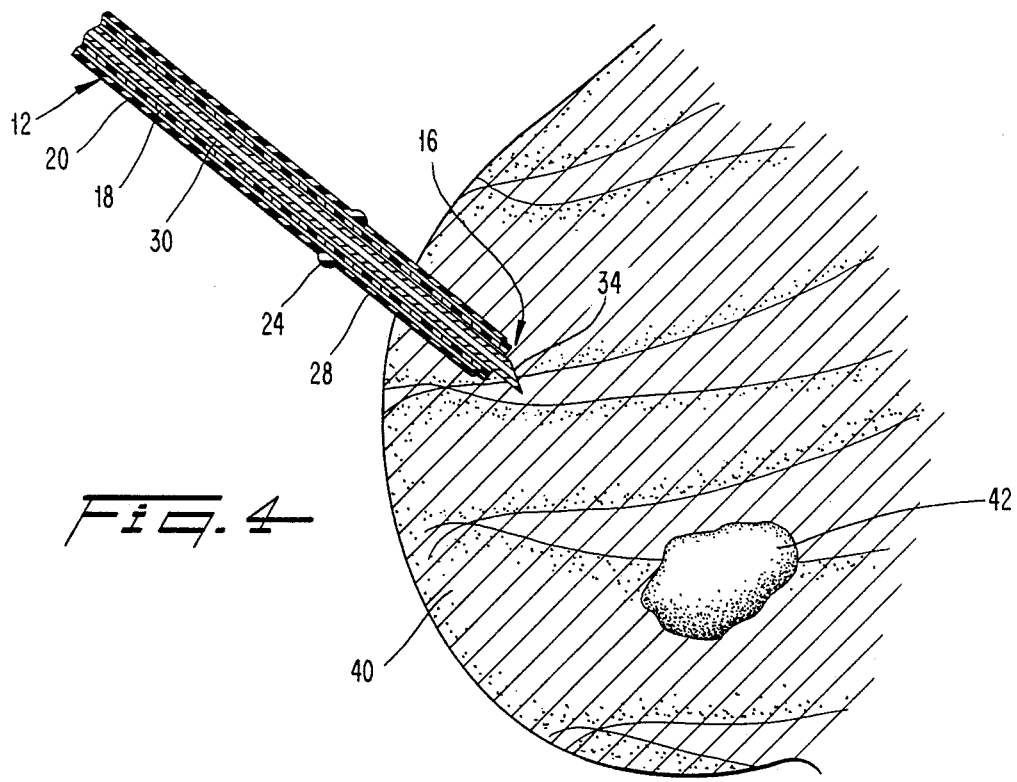
FIGS. 4 and 5 are exaggerated enlarged cross sectional views illustrating initial and final steps in employing the mass localization device of the present invention for locating a mass in breast tissue.

FIGS. 1-3 illustrate the mass localization device of the present invention, generally shown at 10. The localization device 10 includes a rubber catheter 12 having a proximal open end 14 and distal open end 16. The catheter 12 includes an inner wall 18 and an outer wall 20. The inner wall 18 and the outer wall 20 are connected together at proximal end 14 and distal end 16. Between the proximal end 14 and the distal end 16 is a gap 22 located between the inner wall 18 and the outer wall 20.

The inner wall 18 has a substantially uniform cross section along its entire length. The outer wall 20 includes a thickened ring 24 near the distal end 16 of the catheter, which separates the outer wall 20 into a proximal portion 26 and a distal portion 28. The proximal portion 26 has a greater thickness than the distal portion 28, which is more flexible for reasons described hereinafter.

A No. 25 gauge hollow needle 30 is provided having a hub 32 located at the proximal end of the needle 30, and a sharp open distal end 34. The needle 30 has a length slightly greater than the catheter 12. The catheter 12 has a length of 5, 10, 15, or 20 cm, depending on the size of the breast being operated on. The hollow needle 30 is insertable through the proximal end 14 of the catheter 12 so that the sharp distal end 34 extends slightly beyond the distal end 16 of the catheter 12.

The distal portion 28 of the outer wall 20 of catheter 12 forms an inflatable balloon at the distal end 16 of the catheter. A source of fluid, preferably air, 33 is communicated to the balloon 28 via a port 36 provided by a port extension 38 which attaches, or preferably is formed as part of the outer wall 20 of catheter 12. Upon supply of air through port 36, the balloon 28 expands to the position illustrated in FIG. 3, and illustrated in FIG. 2 in phantom at 28'. A preferred diameter of the balloon 28 is 2 to 5 cm. The thickened ring 24 allows only the balloon 28 to expand, rather than both the balloon 28 and the proximal portion 26 of the outer wall 20. When no supply of air is connected to port 36, for expanding the balloon 28, the balloon 28 maintains a flush relationship with the periphery of the catheter 12 as illustrated in FIGS. 1 and 2.

In use, the mass localization device 10 is inserted into body tissue under x-ray control to be adjacent to a mass in the tissue. Once the distal end of the device 10 is located proximate to the mass, local anaesthesia is supplied through needle 30 to the area adjacent the mass. The balloon 28 is then expanded to identify the location of the mass, and the needle 30 is removed. Thereafter, a surgeon can feel the location of the inflated balloon and form an incision from a point on the skin located closest to the balloon so as to make as small an incision as possible to gain access to the mass.

Figure 5:
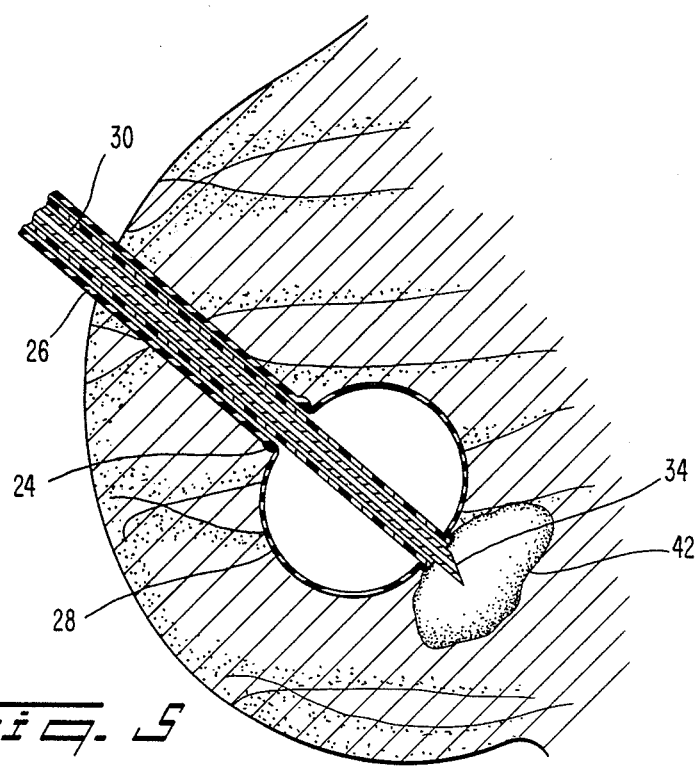

FIGS. 4 and 5 illustrate a localization technique for non-palpable breast masses employing the localization device 10 of the present invention. Initially, the needle 30 is inserted through the catheter 12 so that the distal end of the catheter extends slightly beyond the distal end 16 of the catheter 12. Under x-ray control, the localization device 10 is inserted into the breast tissue 40 and maneuvered towards a mass 42 as illustrated in FIG. 4. The device 10 is carefully moved towards the mass 42 so that the distal end 16 of the catheter 12 is proximate the mass 42 as illustrated in FIG. 5. At this point, local anesthetic is injected through the needle 30 to the suspicious area. Thereafter, the supply of air 33 is connected to the port 36 for inflating the balloon 28 to the position shown in FIG. 5. Now, the mass 42 is palpable since a surgeon can feel the mass 42 through the skin by feeling for the inflated balloon 28. The needle 30 is then withdrawn from the catheter 12 and the patient is prepared for a surgical biopsy or other procedure with the catheter left in place. As a result, the surgeon forms an incision which accurately provides for the most direct access to the mass so that the surgeon can take a biopsy of the suspicious area.

While the localization of breast masses has been specifically described, it is envisioned that the device 10 can be employed for localizing masses in various other tissue environments.

The above description is intended by way of example only, and is not intended to limit the present invention in any way except as set forth in the following claims.

I claim:

1. An apparatus for localizing and palpating a mass in body tissue, said apparatus comprising:
    a flexible catheter having an open proximal end and an open distal end;
    an external sheathing surrounding said catheter and including an expandable balloon portion positioned at a distalmost portion of said distal end of said catheter, said balloon portion being expandable around said catheter at said distalmost portion of said catheter and being inflatable to have a diameter of about 2 to 5 cm at a mass located deeply in the body tissue so as to be palpable through the body tissue so that a direct incision may be made from the skin to the expanded balloon portion across the shortest distance possible for surgically locating the mass with a minimal length incision; and
    a hollow needle having proximal and distal ends, said distal end being sharp, said needle being insertable through said proximal end of said catheter so that said distal end of said needle extends beyond said distal end of said catheter to deliver anaesthesia to an area adjacent to an x-ray identified mass so that said balloon may be inflated under anesthetized conditions to identify the location of the mass by feeling the location of the inflated balloon portion through the body tissue, with means for preventing the distal end of said needle from extending more than slightly beyond said distal end of said catheter.

2. The apparatus of claim 1, further comprising a supply of air connected to said catheter, and said balloon portion being expandable upon receiving air from said supply of air for identifying the mass in the body tissue.

3. The apparatus of claim 1, wherein said catheter includes an inner wall extending along the entire length of said catheter;
    an outer wall forming said external sheathing and being spaced from said inner wall and extending along the entire length of said catheter, said inner wall and said outer wall being connected together at said distal end and proximal end of said catheter, said outer wall including a thickened portion to separate said outer wall into a proximal portion and a distal portion, said proximal portion having a thickness greater than a thickness of said distal portion, and said distal portion of said outer wall forming said expandable balloon portion; and a gap formed between said inner wall and said outer wall extending along substantially the entire length of said catheter and communicating with said distal portion which forms said expandable balloon portion.

4. The apparatus of claim 3, further comprising a port extension member and a supply of air, said port extension member being connected to said catheter for communicating said supply of air to said distal portion which forms said expandable balloon portion via said gap between said inner wall and said outer wall.

5. The apparatus of claim 1, wherein the distal end and the proximal end of said needle are open.

6. An apparatus for localizing and palpating a mass in body tissue, said apparatus comprising:
- a flexible catheter having an open proximal end and an open distal end, said catheter including an inner wall extending along the entire length of said catheter, and an outer wall spaced from said inner wall and extending along the entire length of said catheter, said inner wall and said outer wall being connected at said proximal end and said distal end of said catheter, a gap created between said inner wall and said outer wall extending substantially the entire length of said catheter, said outer wall including distinct proximal and distal portions, said distal portion being located at a distalmost end of said catheter and forming in inflatable balloon;
- a needle having proximal and distal ends, said distal end being sharp, said needle being insertable through said proximal end of said catheter so that said distal end of said needle extends beyond said distal end of said catheter, with means for preventing said distal end of said needle from extending more than slightly beyond said distal end of said catheter;
- a supply of air; and
- a port extension means connected at said outer wall of said catheter for communicating said supply of air to said inflatable balloon via said gap between said inner and outer walls of said catheter, said inflatable balloon being expanded upon receiving air from said supply of air to identify the location of an x-ray located mass by positioning said catheter with said needle located therein adjacent to the mass in the body tissue, said inflatable balloon being inflatable to have a diameter of about 2 to 5 cm at a mass located deeply in the body tissue to be palpable through the body tissue upon expansion so that a direct incision may be made from the skin to the inflatable balloon across the shortest distance possible for surgically locating the mass with a minimal length incision.

7. The apparatus of claim 6, wherein said proximal portion of said outer wall has a first thickness, and said distal portion of said outer wall has a second thickness, said first thickness being greater than said second thickness for ensuring that said distal portion of said outer wall expands upon supply of air to said inflatable balloon.

8. The apparatus of claim 7, further comprising a thickened ring member at an interface of said proximal portion and said balloon of said outer wall for preventing said proximal portion from inflating with said balloon upon supply of air.

* * * * *